United States Patent [19]

Ramspeck et al.

[11] 4,455,156
[45] Jun. 19, 1984

[54] PROCESS FOR IMPROVING THE GAS SEPARATION IN LIQUID/GAS REACTORS

[75] Inventors: Wolfgang Ramspeck, Oberursel; Wolfgang Sittig, Hofheim am Taunus, both of Fed. Rep. of Germany

[73] Assignee: Hoechst Aktiengesellschaft, Frankfurt am Main, Fed. Rep. of Germany

[21] Appl. No.: 183,448

[22] Filed: Sep. 2, 1980

[30] Foreign Application Priority Data

Sep. 4, 1979 [DE] Fed. Rep. of Germany ....... 2935639

[51] Int. Cl.$^3$ .............................................. B01D 19/00
[52] U.S. Cl. ............................................................ 55/52
[58] Field of Search .................. 55/52, 185, 186, 196, 55/233, 234; 210/617, 618, 629, 758, 150, 151, 195.3, 195.4, 196, 197, 220, 221.1

[56] References Cited

U.S. PATENT DOCUMENTS

| | | | |
|---|---|---|---|
| 2,518,845 | 8/1950 | Williams | 55/208 X |
| 2,764,533 | 9/1956 | Oetjen et al. | 55/52 X |
| 3,377,778 | 4/1968 | Gaertner | 55/208 X |
| 3,626,670 | 12/1971 | Pecker | 55/159 |
| 3,648,438 | 3/1972 | Arbogast | 55/196 X |
| 3,826,739 | 7/1974 | Kubo et al. | 210/758 X |
| 3,966,599 | 6/1976 | Burkhead | 210/618 |
| 3,966,608 | 6/1976 | Mason et al. | 210/151 |
| 4,166,730 | 9/1979 | Warhol | 55/233 X |

FOREIGN PATENT DOCUMENTS

| | | |
|---|---|---|
| 1805360 | 5/1970 | Fed. Rep. of Germany . |
| 2173042 | 10/1973 | France . |
| 2274346 | 1/1976 | France . |
| 1491502 | 11/1977 | United Kingdom . |
| 269030 | 12/1968 | U.S.S.R. . |

Primary Examiner—Robert H. Spitzer
Attorney, Agent, or Firm—Curtis, Morris & Safford

[57] ABSTRACT

Apparatus and process for ensure the coalescence and separation of fine gas bubbles in the degassing zone of liquid/gas tube or loop reactors. The invention is not limited to these two types of reactors. A liquid/gas current is introduced into a layer of solid particles whose size, density, and shape are chosen such that their sedimentation speed is greater than the speed of the rising liquid/gas mixture, and the fluidization point speed is selected to be less than the liquid speed.

3 Claims, 4 Drawing Figures

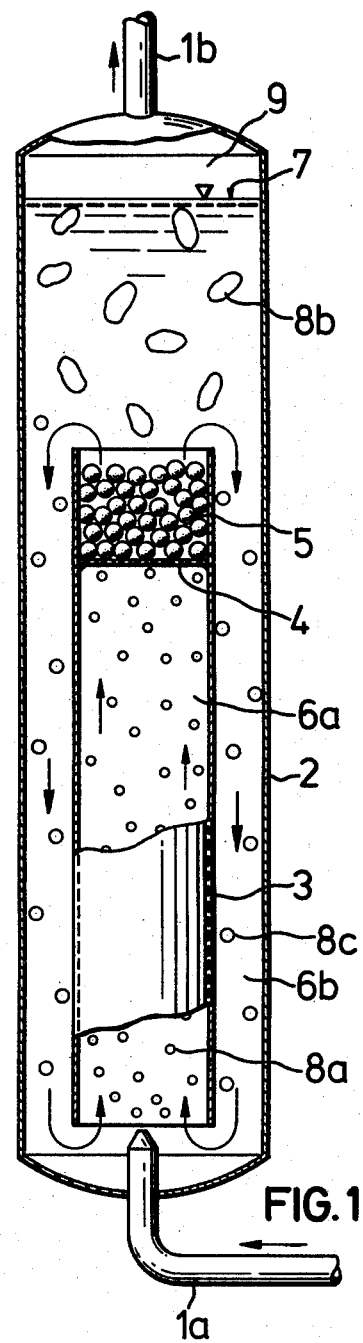
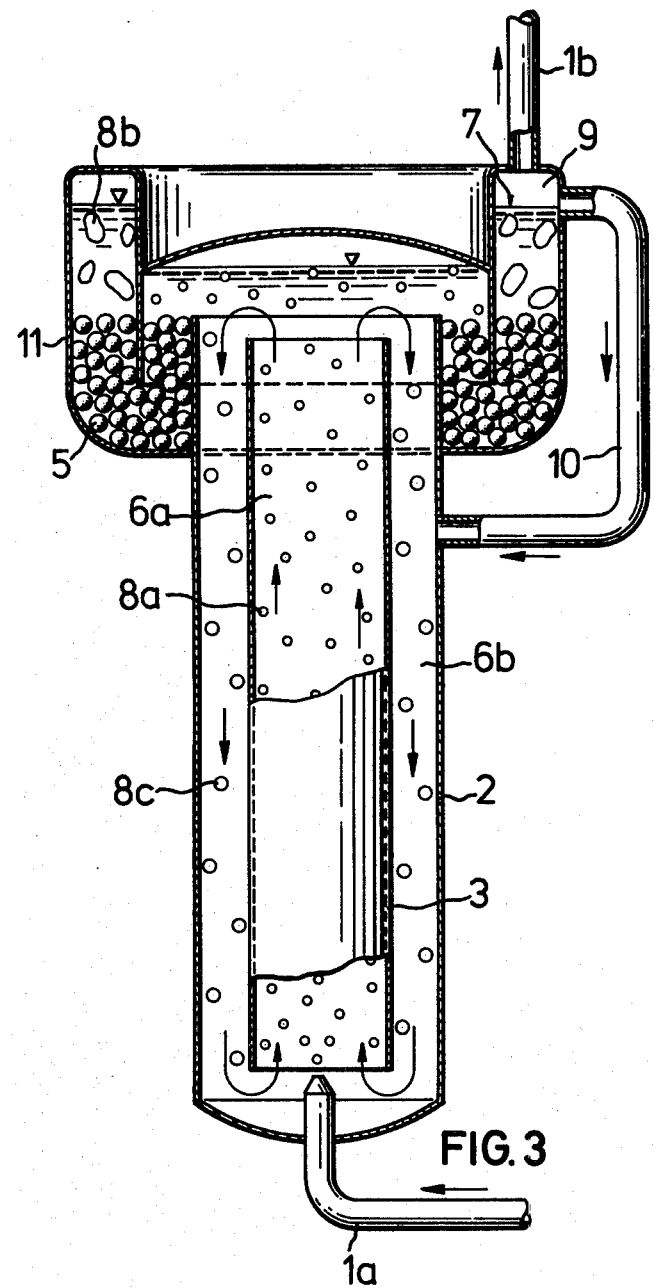

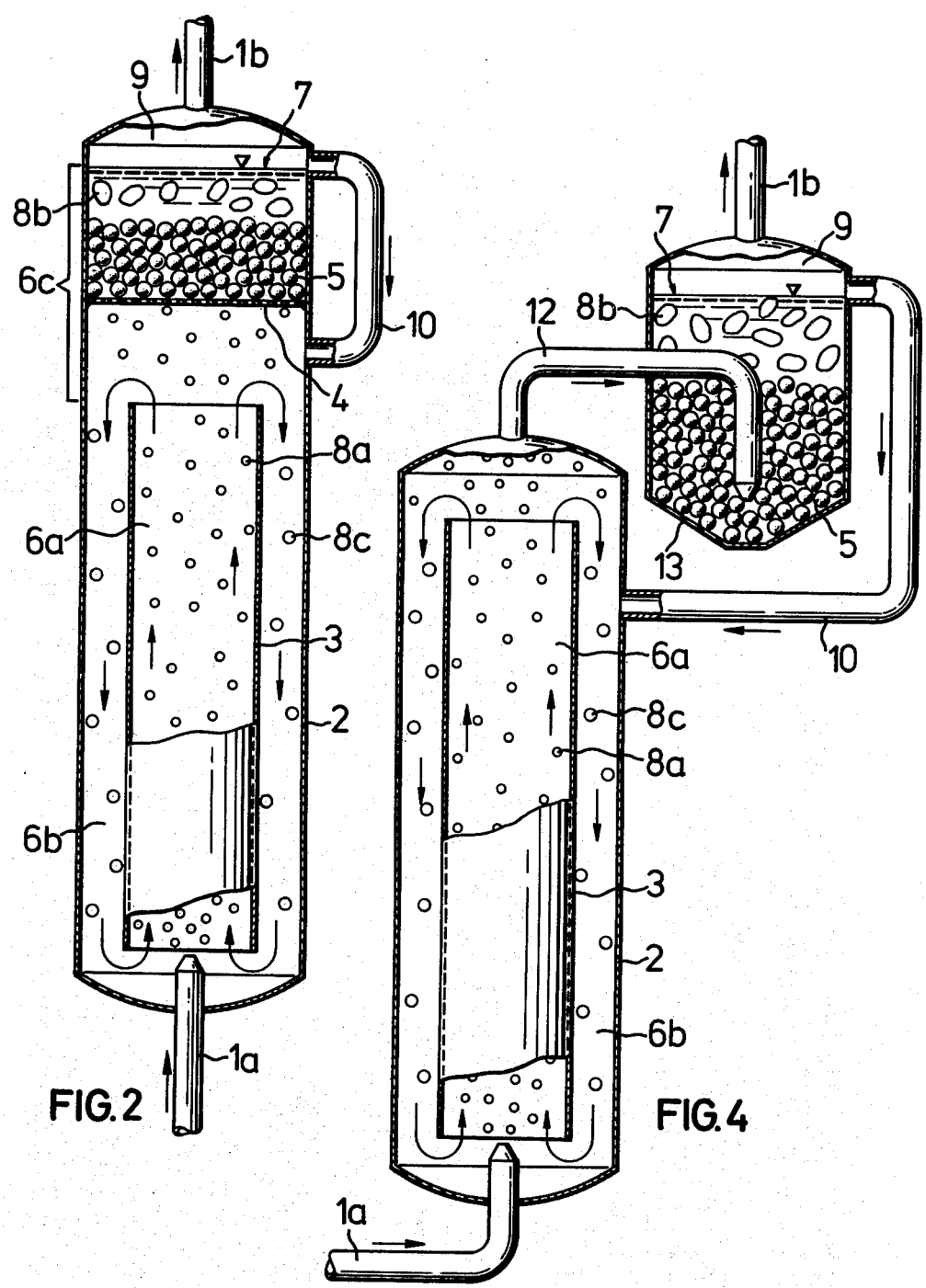

PROCESS FOR IMPROVING THE GAS SEPARATION IN LIQUID/GAS REACTORS

BACKGROUND OF THE INVENTION

1. Field of the Invention

This invention relates to liquid/gas reactors, such as loop or tube reactors. More particularly, this invention is directed to method and apparatus for enhancing the separation of gas bubbles from the liquid phase.

2. Brief Description of the Prior Art

For separating the gas phase in liquid/gas reactors, cyclones, foam separators, demisters and similar equipment are conventionally used to present a large surface at large volume. Such liquid/gas reactors are often provided with a packing layer and/or operated as fluidized bed reactors in order to increase the phase interface.

On the basis of tests on such reactors, phenomenological descriptions of bubble size alterations in fluidized beds and/or packing layers have been published.

OBJECTS AND SUMMARY OF THE INVENTION

It is an object of the invention to provide a process and apparatus for improving the gas separation in liquid/gas reactors.

In accordance with an aspect of the invention, a process is provided for improving the coalescence and separation of fine gas bubbles in the degassing zone of liquid/gas reactors, wherein the liquid/gas current is introduced into a layer of solid particles acting as fluidized bed having an greater specific weight than the liquid/gas mixture a density of from 0.5 to 13 g/cm$^3$ and a nominal size of from 0.1 to 100 mm; the solid particles being chosen so that their size, density, and shape ensure that their sedimentation velocity is higher than the speed of the liquid/gas mixture relative to the free reactor cross-section (i.e., liquid speed), and that on the other hand the fluidization point speed necessary for their fluidization is less then the cited liquid speed.

In accordance with an aspect of this invention, the coalescence and separation of fine gas bubbles is enhanced thereby improving the operation of a liquid-gas reactor, such as a loop reactor. Gas is introduced into the liquid-gas mixture at a lower portion thereof and the mixture rises in an inner tube. Separated liquid then settles in an annular outside the inner tube. The rising liquid-gas mixture is passed through a layer of solid particles, which are selected in matetial, size, and weight so that the rising liquid-gas current causes them to form a fluidized bed. The size, density, and shape of the particles are such that their sedimentation velocity is somewhat higher then the speed of the upward liquid-gas current, while the speed of the liquid-gas current is higher than that required for their fluidization. The particles can be selected in a rather wide range of nominal sizes (0.1 to 100 mm) and densities (0.5 to 13 g/cm$^3$).

Advantageously, the layer of solid particles is arranged on a support which may be a sieve plate, a grate, or a wire cloth.

The invention will be better understood by reference to the accompanying drawings.

BRIEF DESCRIPTION OF THE DRAWINGS

FIG. 1 shows a first embodiment of a reactor according to this invention having an arranged layer of solid particles for improving gas separation from the liquid phase.

FIG. 2 shows a second embodiment of a reactor according to this invention using a bubble cap column atop a loop reactor.

FIG. 3 shows a third embodiment of a reactor according to this invention using a continuous annular stage atop a loop reactor.

FIG. 4 shows a fourth embodiment of a reactor according to this invention with a gas separator stage coupled outside a loop reactor.

DETAILED DESCRIPTION OF SEVERAL PREFERRED EMBODIMENTS

With reference to the drawings, in which like reference characters identify similar elements which will be described in detail only with respect to the reactor with which they are first introduced, FIG. 1 shows a loop reactor 2. Gas is fed thereto through a gas inlet 1a at the bottom thereof and is taken off from the top by a gas outlet 1b. Disposed concentrically within the reactor 2 is an inner tube 3 having a porous or mesh support 4 (e.g., a sieve plate or grate) across the upper part thereof to support a layer of solid particles 5.

The wall of the loop reactor 2 and the tube 3 define an upstream zone 6a within the tube 3 and a downstream zone 6b in the annulus between the wall of the reactor 2 and the tube 3.

The reactor is filled with a liquid-and-gas mixture up to a liquid level 7, with a gas space 9 between such level 7 and the gas outlet 1b.

Gas is injected from the inlet 1a into the mixture in the form of small bubbles 8a which rise uncoalesced within the upstream zone 6a. The flow rate upward of the mixture more or less corresponds to the size of the uncoalesced bubbles 8a. These bubbles 8a pass upward through the support 4 and particles 5. The latter serve to increase the coalescence of the fine gas bubbles, and resulting coalesced large bubbles 8b which develop therein rise to the gas space 9. A small amount of remaining smaller coalesced gas bubbles 8c then enter the downstream zone 6b. These bubbles 8c fail to rise because their rate of ascension is less than the liquid speed in the downstream zone 6b. However, these bubbles 8c again cycle into the upstream zone 6a and eventually are coalesced in the layer of particles 5.

FIG. 2 shows an alternate embodiment of this invention wherein the tube 3 is open and the support 4 and layer of solid particles 5 extend across a bubble cap column 6c. An exterior recycling duct 10 is provided for the liquid phase to return from the liquid level 7 to a point below the support 4. This ensures recycling of the liquid through the layer of solid particles 5 when there is high gas pressure.

FIG. 3 shows another embodiment of this invention wherein a continuous annular space 11 is disposed atop the reactor 2. Here the particles 5 are held in the annular space 11 and a porous support 4 is unnecessary. The liquid containing uncoalesced gas bubbles 8a passes from the top of the reactor 2 downward into the particles 5 and then upward at the outer part of the annular space 11. The coalesced bubbles 8b rise to the gas space in the top of the annular space 9 and liquid is returned through the recycling duct 10 from the liquid level 7 to the downstream zone 6b.

FIG. 4 shows still another embodiment of this invention in which the solid particles 5 are contained in an external gas separator 13. A dip pipe 12 extends from the reactor top into the particles 5 to inject the liquid and uncoalesced bubbles 8a. The liquid recycling duct 10 returns the liquid from the gas separator 13 to the downstream zone 6b of the reactor 2. While the gas separator 13 is shown with a tapered bottom, it could have any convenient shape; for example, the separator 13 could be a cylindrical vessel with a flat, bumped, or half-round bottom.

In principle, the process of the invention for improved gas separation can be applied not only in a loop reactor, but also in any other two-phase reactor, for example a bubble-cap column reactor, an agitator vessel reactor or a tube reactor. In these cases, the layer of solid particles is arranged in the degassing zone.

The density of the solid particles to be used in accordance with the invention is from about 0.5 to about 13 $g/cm^3$, in aqueous systems preferably about 1.1 to about 4 $g/cm^3$. Suitable materials are for example ceramic materials, glass, plastics, metals or metal alloys. Advantageously, the material used should be immune to abrasion or to subject to abrasion only to an insignificant extent so that the quality of the product is not adversely affected.

The solid particles may have any of the shapes which are usual for the hitherto applied packings; preferably, they are superoids, i.e., ball-shaped or lenticular. The nominal size (the diameter in the case of balls) is in the range of from about 0.1 to 100 mm.

For shape, density and size of the particles, as aforesaid the speed ratios in the liquid/gas mixture present in the case in question are controlling as to particle selection.

The height of the fluidized bed (layer of solid particles) is preferably 0.2 to 3 times that of its largest diameter.

In the case of slightly foaming media (e.g., in a fermentation process) it is advantageous to introduce an anti-foaming agent into the zone of the fluidized bed.

The process of the invention is suitable for an improved separation of solutions, suspensions, or emulsions, for example catalyst suspensions, or fermentation culture suspensions.

The following examples illustrate the invention.

(1) COMPARATIVE EXAMPLE

In a loop reactor (operated according to the principle of an airlift pump) having a diameter of 300 mm, a height of 4 m and a diameter of the inner tube of 200 mm, provided with a bubble-cap column mounted on its top, a fermentation culture suspension (Methylomonas clara) was grown in a nutrient medium composed as follows:

$H_3PO_4$; 85% strength: 1.9 l per 1000 l water
$NH_4OH$, 25% strength: 2.8 l per 1000 l water
$K_2SO_4$: 1.4 kg per 1000 l water
$MgSO_4.7H_2O$: 0.9 kg per 1000 l water
$Na_2SO_4$: 0.25 kg per 1000 l water
$CaCO_3$: 0.14 kg per 1000 l water
$Fe_2(SO_4)_3.3H_2O$: 0.085 kg per 1000 l water
trace element solution: 1.0 l per 1000 l water.

The gas content (air content) of the liquid/gas mixture was 13%, and the oxygen charge was 6.4 $kg/m^3.h$. The bumping surface and the height of rise of the liquid elements hurled up proved that the limit of gas stress was attained with the adjusted gas speed in the empty tube of 0.15 m/s. The insufficient gas separation did not allow any increase of gas stress because of foam formation.

(2) EXAMPLE ACCORDING TO THE INVENTION

In the bubble-cap column of the apparatus combination of reactor and column according to Example 1, a sieve plate was inserted (as shown in FIG. 2 of the drawings), and a layer having a height of 150 mm (measured in static position) of ceramic balls having a density of 2.7 $g/cm^3$ and a diameter of 12 mm was introduced. Nutrient medium, gas content and dimensions of the loop reactor were as indicated in Example 1. The gas speed in the empty tube was 20% higher than that of Example 1. The oxygen charge was 7.8 $kg/m^3.h$.

Of course, the invention is not limited to the foregoing embodiments and example, which are intended to be illustrative of the invention. Many possible modifications and variations of these will be apparent to persons of ordinary skill without departing from the scope and spirit of the invention, which is to be measured by the appended claims.

What is claimed is:

1. A process for improving the coalescence and separation of fine gas bubbles of a liquid-gas mixture in a liquid-gas reactor, comprising introducing a gas into the mixture at a lower portion thereof so that the liquid-gas mixture rises at a liquid speed as a liquid-gas current; and passing the liquid-gas current upward through a layer of solid particles in said current to form a fluidized bed, the density of the fluidized bed being greater than that of the liquid-gas mixture; wherein the said solid particles have a density of 0.5 to 13 $g/cm^3$ and a nominal size of 0.1 to 100 mm; with the size, density, and shape thereof being selected so that the particles have a sedimentation velocity which is higher than said liquid speed, and so that said liquid speed is higher than that necessary for their fluidization 2. The process as claimed in claim 1, wherein the height of the fluidized bed is 0.2 to 3 times that of its largest diameter.

3. The process as claimed in claim 1 or 2, wherein an anit-foaming agent is introduced into the fluidized bed.

* * * * *